United States Patent
Black et al.

(10) Patent No.: US 10,286,207 B2
(45) Date of Patent: May 14, 2019

(54) FLANGED SELF-CLOSING MICROCHANNEL ARRAY

(71) Applicants: Iian Black, Boca Raton, FL (US); Ranu Jung, Coral Gables, FL (US)

(72) Inventors: Iian Black, Boca Raton, FL (US); Ranu Jung, Coral Gables, FL (US)

(73) Assignee: THE FLORIDA INTERNATIONAL UNIVERSITY BOARD OF TRUSTEES, Miami, FL (US)

( * ) Notice: Subject to any disclaimer, the term of this patent is extended or adjusted under 35 U.S.C. 154(b) by 0 days.

(21) Appl. No.: 15/730,892

(22) Filed: Oct. 12, 2017

(65) Prior Publication Data

US 2018/0099139 A1 Apr. 12, 2018

Related U.S. Application Data

(60) Provisional application No. 62/407,266, filed on Oct. 12, 2016.

(51) Int. Cl.
| | |
|---|---|
| *A61N 1/05* | (2006.01) |
| *A61B 5/00* | (2006.01) |
| *A61B 5/04* | (2006.01) |

(52) U.S. Cl.
CPC ........ *A61N 1/0556* (2013.01); *A61B 5/04001* (2013.01); *A61B 5/4851* (2013.01)

(58) Field of Classification Search
CPC .............. A61N 1/0556; A61B 5/04001; A61B 5/4851; F16B 7/0433
See application file for complete search history.

(56) References Cited

U.S. PATENT DOCUMENTS

| | | | | |
|---|---|---|---|---|
| 2,997,531 | A * | 8/1961 | Oldham | F02P 7/025 174/158 R |
| 3,266,761 | A * | 8/1966 | Walton | F16L 3/1207 174/159 |
| 9,853,436 | B2 * | 12/2017 | Simon | H02G 7/12 |
| 2010/0168831 | A1 * | 7/2010 | Korivi | A61N 1/0556 607/118 |
| 2010/0298916 | A1 * | 11/2010 | Rabischong | A61N 1/0556 607/116 |
| 2011/0071590 | A1 * | 3/2011 | Mounaim | A61N 1/36007 607/41 |
| 2016/0279438 | A1 * | 9/2016 | Simons | A61N 5/0601 |

* cited by examiner

*Primary Examiner* — Mark Bockelman
(74) *Attorney, Agent, or Firm* — Saliwanchik, Lloyd & Eisenschenk

(57) ABSTRACT

Devices and methods for implanting neural interface technology in mammals are provided. A device can include an array of self-closing channels; two flanges that flank the array of channels, the flanges can be used to open the self-closing channels; and a plurality of cuff electrodes disposed at a circumference of each self-closing channel, the plurality of cuff electrodes being optimally disposed to detect a maximum amplitude of an action potential signal.

12 Claims, 13 Drawing Sheets

FLANGED SELF-CLOSING MICROCHANNEL ARRAY

CROSS-REFERENCE TO RELATED APPLICATIONS

This application claims the priority benefit of U.S. Provisional Application Ser. No. 62/407,266, filed Oct. 12, 2016, which is incorporated herein by reference in its entirety.

BACKGROUND

The human peripheral nervous system relies on large amounts of sensory feedback to modulate the neural drive to organs and limbs. A disruption or loss of sensory feedback, for example through injury or illness, results in inappropriate motor commands to different body systems and a subsequent loss of normal function.

Certain technologies exist for stimulating nerves after feedback has been lost or disrupted. For example, cuff stimulators have been implanted in humans to prevent foot drop for those with hemiplegia, restore grip functionality for those with paralyzed hands, and restore elective voidance in individuals with incontinence following spinal cord injury. However, no platform currently exists to enable human amputees to achieve intuitive control of advanced upper-limb prostheses.

Additionally, many implantable neural interface technologies for stimulating nerves lack feedback from sensory systems in order to improve their neural activity modulation. This can be because of the difficulty in recording the small electrical signals generated by nerve axons.

The ability to effectively record the electrical signals from sensory nerves could be used to appropriately modulate neural systems and move functional restoration towards pre-injury levels. One promising technology—microchannel electrode arrays—has emerged, which fares well in the body environment without causing neural damage, and also records nerve signals at high signal-to-noise ratios. In rodent models, for example, high signal-to-noise ratio recordings bladder and cutaneous afferents have been obtained using dissected portions of lumbar roots implanted in microchannel electrode arrays.

One drawback of the current microchannel arrays used in animal experiments, however, is that they require gluing a separate silicone cover plate to the top of the array to seal, and electrically isolate, nerve strands in different channels. This technique may result in incomplete compartmentalization of nerves within their channels because there may be gaps between the top surface of the array and the bottom surface of the installed cover plate. In turn, this increases the likelihood of unwanted cross-talk, or electrical coupling, between adjacent microchannels, which compromises the functionality of the device. Cross-talk reduces the devices ability to discriminate neural activity in one channel from that occurring in adjacent channels.

Another drawback with current technology is damage to neural tissue during surgery. For example, axonal damage and cell death can result from neural inflammation caused by surgical trauma during the implantation of nerves into microchannels or cuffs.

Cuff electrodes can be distinguished among neural interfaces as one of the few types of electrodes capable of establishing long-term electrical connectivity with peripheral nerves. They can be used to monitor neural activity in animals and to treat neurological impairment in humans.

A need exists for improved technology to aide in the modulation of nervous system functioning in subjects with compromised neural function, which reduces the detrimental effects of surgical trauma while improving long-term function of nerves.

BRIEF SUMMARY

Embodiments of the subject invention provide devices and methods for implanting nerves in a subject.

In an exemplary embodiment, the device comprises a flanged microchannel array with self-closing channels. In specific embodiments, the claimed device comprises up to three or more tube-like self-closing channels defined by a wall of uniform thickness, wherein the channels can be aligned in a parallel fashion and flanked by two flanges, and, further, wherein each of the channel walls contains a longitudinal slit.

In another embodiment, the present invention provides a method of implanting nerves in a mammalian subject using the claimed device. The method may comprise the steps of simultaneously aligning separate nerve strands over each of the closed channels; applying equal and opposite tension to the two flanges, causing the channels to open simultaneously; introducing each nerve into one of the open channels so each of the nerves lies completely within a channel; and releasing the tension on each flange to enable the channels to self-close.

An aspect of the present invention allows for reduction in nerve tissue damage as a result of excess manipulation during surgical procedures. The present invention can also help improve long-term function of implanted nerves in subjects.

In another embodiment, the present invention provides methods of producing the claimed device. For example, the device can be produced by hand using off-the-shelf materials, or by automated manufacturing processes.

DETAILED DESCRIPTION

To meet the need for improved methods of stimulating nerves to enhance and/or restore neural function, provided herein is a device for implanting nerves in mammals, and methods of using and making the same.

In an exemplary embodiment, the device comprises a flanged microchannel array with self-closing channels. In specific embodiments, the claimed device comprises tube-like self-closing channels, which can be defined by a wall of uniform thickness, wherein the channels can be aligned in a parallel fashion and flanked by two flanges, and, further, wherein each of the channel walls contains a longitudinal slit.

Figures 2A, 2B:
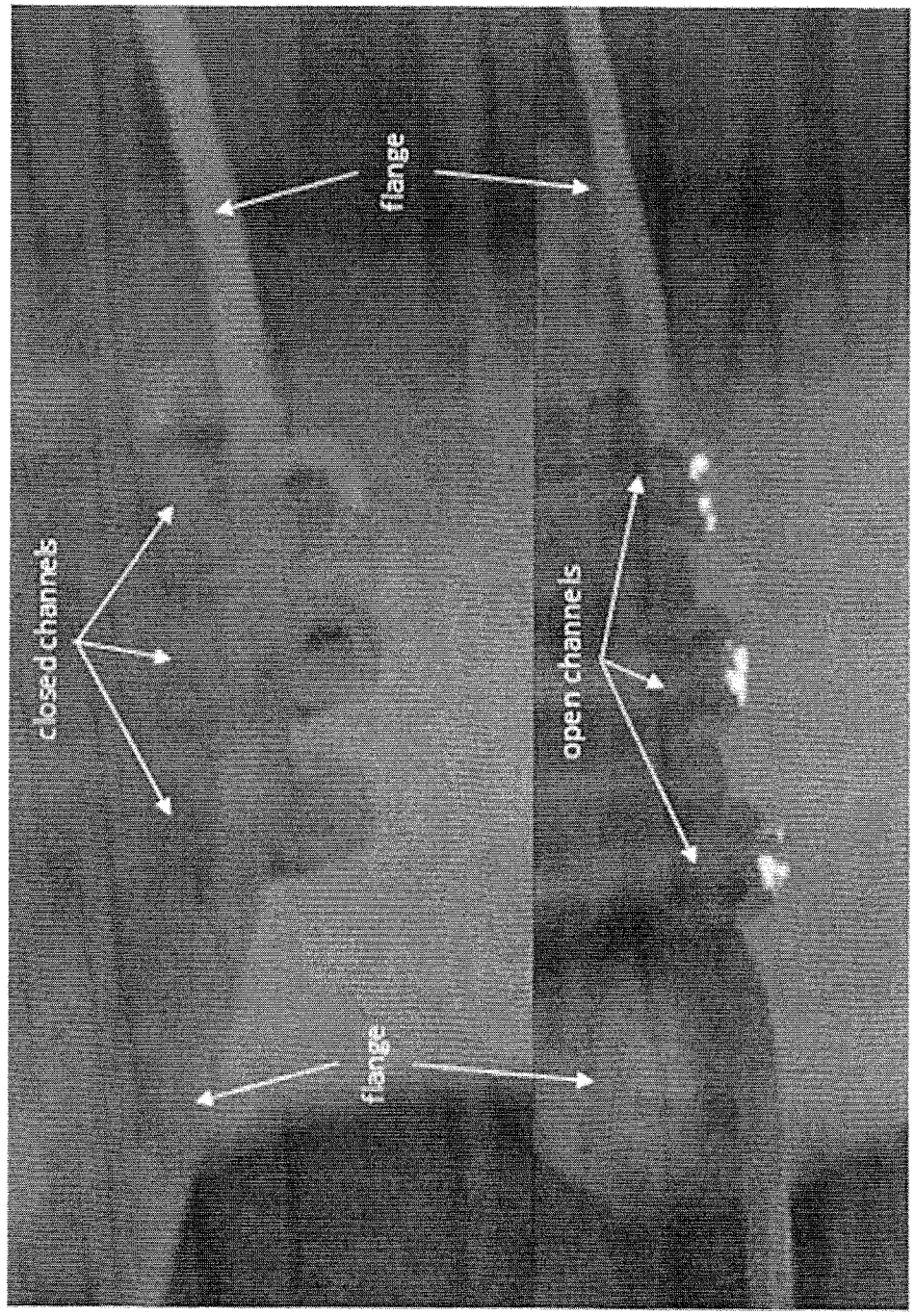
FIG. 2A shows an illustration of a triplet array with all channels in their naturally closed state, according to an embodiment of the invention.
FIG. 2B shows a triplet array with all channels simultaneously open when flanges are pulled, according to an embodiment of the invention.

FIGS. 2A and 2B generally show the claimed device. FIG. 2A shows an array comprising three parallel channels, or a "triplet" array, with all channels in their naturally "closed" state. Each channel contains a longitudinal slit in the channel wall, as depicted by the arrows labelled "closed channels" The arrows labelled "flange" depict the array of parallel channels flanked on either side by two flanges.

FIG. 2B shows the device in its "open" state. As depicted by the three arrows labelled "open channels," the device is "open" when the flanges can be pulled in opposite directions, thus forming exposed cavities wherein nerve strands can be introduced.

The dimensions of the microchannels of the claimed device can be any suitable dimension for receiving the nerve or nerves to be repaired and/or implanted. For example, in one embodiment, the closed channels can have an internal diameter of about 50 µm to about 500 µm. In another embodiment, microchannel wall width can range from about 20 µm to about 100 µm. In yet another embodiment, microchannel lengths can range from about 1 mm to about 10 mm.

In one embodiment, the present invention provides a method of implanting nerves in a mammalian subject using the claimed device, comprising the steps of aligning separate nerve strands over each of the closed channels; applying approximately equal and opposite tension to the two flanges, causing the channels to open simultaneously; introducing each nerve into one of the open channels so each of the nerves lies completely within a channel; and releasing the tension on each flange to enable the channels to self-close.

Figure 1A:
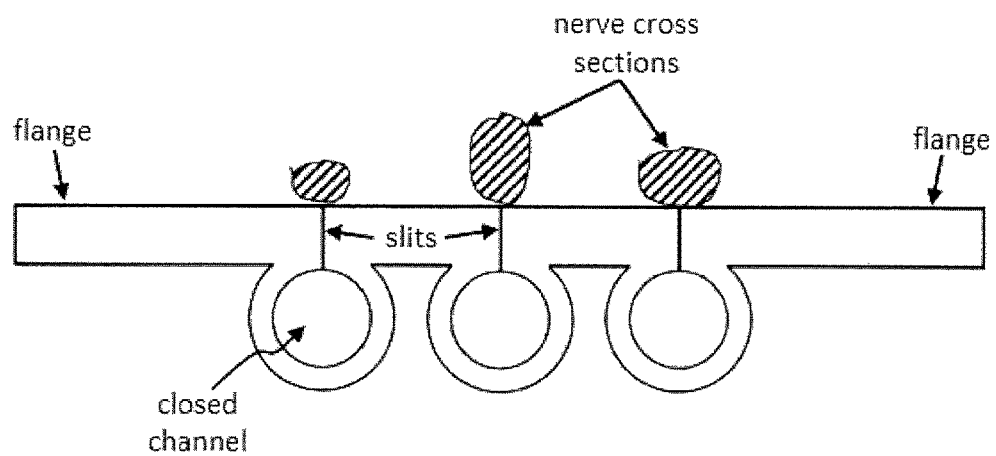
FIG. 1A-1C show a schematic of a cross-sectional view of a three-channel, or "triplet," array and the technique for inserting nerves into the channels, according to embodiments of the invention.
Figure 1B:
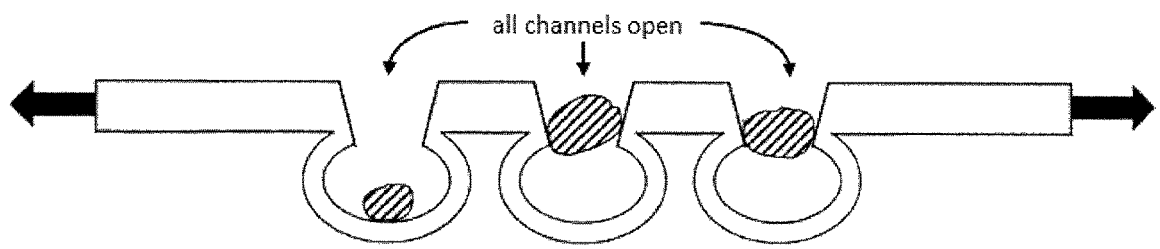
Figure 1C:
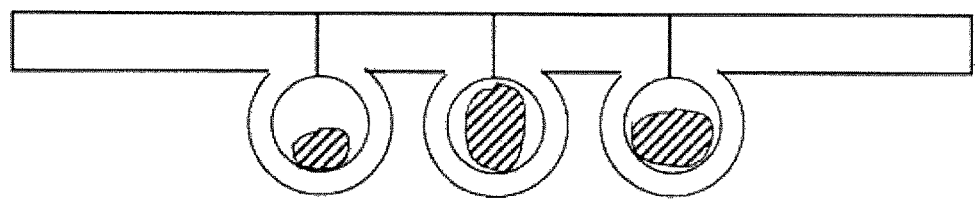

FIGS. 1A-1C provide the general technique for inserting nerves into the claimed device. Shown is a schematic cross-sectional view of a triplet array. According to the present invention, once nerves (shaded) have been approximately aligned with channel slits (FIG. 1A), all of the channels can be opened simultaneously by pulling the flanges apart (bold arrows), which enables the nerves to work their way into the exposed cavities with a minimum amount of manipulation (FIG. 1B). Channels automatically close around captured nerves when the flanges are released (FIG. 1C).

The present invention allows for reduction in nerve tissue damage as a result of excess manipulation during surgical procedures. A flanged microchannel array with self-closing channels enables multiple nerve strands to be aligned and implanted into all channels of the array simultaneously with a minimal amount of neural manipulation. In reducing the amount of manipulation required, deleterious effects of surgical trauma can be reduced.

Another aspect of the present invention allows for easier electrical isolation between microchannels. By using self-closing channels, the claimed device eliminates the need for a cover plate to achieve electrical isolation.

Furthermore, self-closing channels might ordinarily be more difficult for implanting nerves when compared to channels that are open by design, as the surgeon must open the channel while simultaneously attempting to maneuver the nerve into the open region of the channel. However, the use of flanges in the present device mitigates this concern. All channels can be opened along their entire lengths simply by pulling on the flanges with enough force to overcome the closing tendency of the channels. Once this has been achieved, nerves may easily be maneuvered into each channel with a minimum amount of surgical manipulation. By reducing the risk of nerve trauma and facilitating nerve insertion, the device facilitates adoption of neural interfaces by surgeons and practitioners who treat neurological conditions.

In another embodiment of the present invention, the claimed device and methods can be used to enhance the capability of current neurostimulation systems by providing a viable interface to record electrical signals from sensory nerves, thus providing feedback to achieve closed-loop control of current neuroprosthetic systems.

Embodiments of the subject invention can further comprise microfluidics for nutrient and growth factor delivery into the microchannels of the device.

Embodiments of the subject invention can further comprise use of an acellular nerve graft in the microchannels to increase and stabilize axon regeneration into the microchannels of the device.

Embodiments of the subject invention can be manufactured using porous material for increased nutrient exchange into the microchannels of the device Embodiments of the subject invention can further comprise chemical and/or biological factors to increase and stabilize regeneration. Examples include, among others, laminin, chondroitinase and/or nerve growth factor (NGF). These factors additionally could be contained within degradable or non-degradable hydrogels, nanoparticles or other encapsulants.

Embodiments of the subject invention can further comprise chemical and/or biological factors to allow the separation of motor and sensory axons. This would allow certain microchannels to house motor axons and other microchannels to house sensory axons that could then be interfaced with in a more specific manner.

Embodiments of the subject invention can further comprise cells including stem cells and/or Schwann cells into the microchannels for increasing and stabilizing axon regeneration.

The present invention can be used in neural prosthetic interfacing, allowing amputees to control a prosthetic device by recording from nerves and acquire sensation from the prosthetic device by stimulating nerves. This includes prosthetic limbs and retinal prosthetics among others. The device could be implanted in peripheral nerves, the spinal cord, and/or the optic nerve.

The present invention can be used in functional electrical stimulation (FES), allowing individuals suffering from various disabilities to regain function. This includes individuals suffering from many types of paralysis stemming from a spinal cord injury and could restore limb movements as well as bowel and bladder control. This can alleviate individuals suffering from the 'foot drop' syndrome.

The present invention can be used in conduction blocking, allowing for pain modulation by controlling nerves that are conducting pain signals to the brain or that have aberrant activity resulting in pain signals.

The present invention further can be used as a tool by researchers and scientists to determine function of nerves and axons as they relate to various sensory and/or motor functions. Additionally, the present invention can be used to study how axons behave and how they interact with other tissues, change over time and after an injury. The present device, in conjunction with tools to assess cortical activity, can also be used to study how information in the periphery as coded by axons is translated to cortical activity.

The present invention can be used in measuring impedance, allowing doctors to monitor nerve regeneration in an individual with nerve damage. This would allow doctors to monitor bone regeneration in an individual with a bone fracture, and to monitor skin regeneration/growth in the subdural layers not visible to the human eye.

Embodiments of the subject invention can further comprise a plurality of electrodes in each channel. The additional electrode(s) can be used as a reference electrode, for unidirectional stimulation, and for stimulation and conduction blocking purposes in conjunction with each other.

Embodiments can further comprise an electrical shielding cage or wire-like structure around the implant to serve a purpose similar to that of a Faraday cage and reduce noise and/or disruptive electromyogram (EMG) signals from muscles.

An expression for predicting the extracellular potentials generated by myelinated fibers enclosed in a similar channel can be as follows:

$$v(x) = -\frac{R_e}{R_i}\left[V(x) - \left(1 - \frac{x}{L}\right)V(0) - \left(\frac{x}{L}\right)V(L)\right] = -\frac{R_e}{R_i}[2nd\ Diff] \quad (1)$$

where v(x) is the extracellular potential at axial position x, V(x) is the transmembrane potential of the active fiber within the channel at position x, V(0) and V(L) are the transmembrane voltages at the channel's entrance and exit, respectively, L is the channel length, $R_e$ is the longitudinal resistance of the extracellular media surrounding the active fiber, and $R_i$ is the longitudinal resistance of the active fiber's axoplasm.

The bracketed term in (1) will herein be referred to as the "$2^{nd}$ Difference" term. The coefficient on the $2^{nd}$ Difference term reverses the polarity of the $2^{nd}$ Difference and scales it by a ratio of the extra-axonal to the intra-axonal longitudinal resistances. This ratio can be proportional to the square of the ratio of the diameter of the active fiber to the diameter of the channel and can be less than 1 since the diameter of the axon to be recorded can be orders of magnitude smaller than the channel (or cuff) containing the nerve bundle in which the axon resides. The cross-sectional area of the active fiber to that of the channel may be considered to remain invariant. 2.2. A graphical representation of the $2^{nd}$ Difference motivates an in-depth analysis of the effect of electrode position on signal amplitude The $2^{nd}$ Difference term in (1) can be re-expressed as:

$$2nd\ Diff = V(x) - \left(\frac{V(L) - V(0)}{L}x + V(0)\right) \quad (2)$$

The expression in curved brackets represents the last two terms in (1) as a line connecting the amplitudes of the transmembrane potential at the ends of the channel. Thus, the $2^{nd}$ Difference may be computed at any longitudinal position x within the channel by subtracting the height of this connecting line at x from the value of the transmembrane voltage at x, V(x).

Figure 5A:
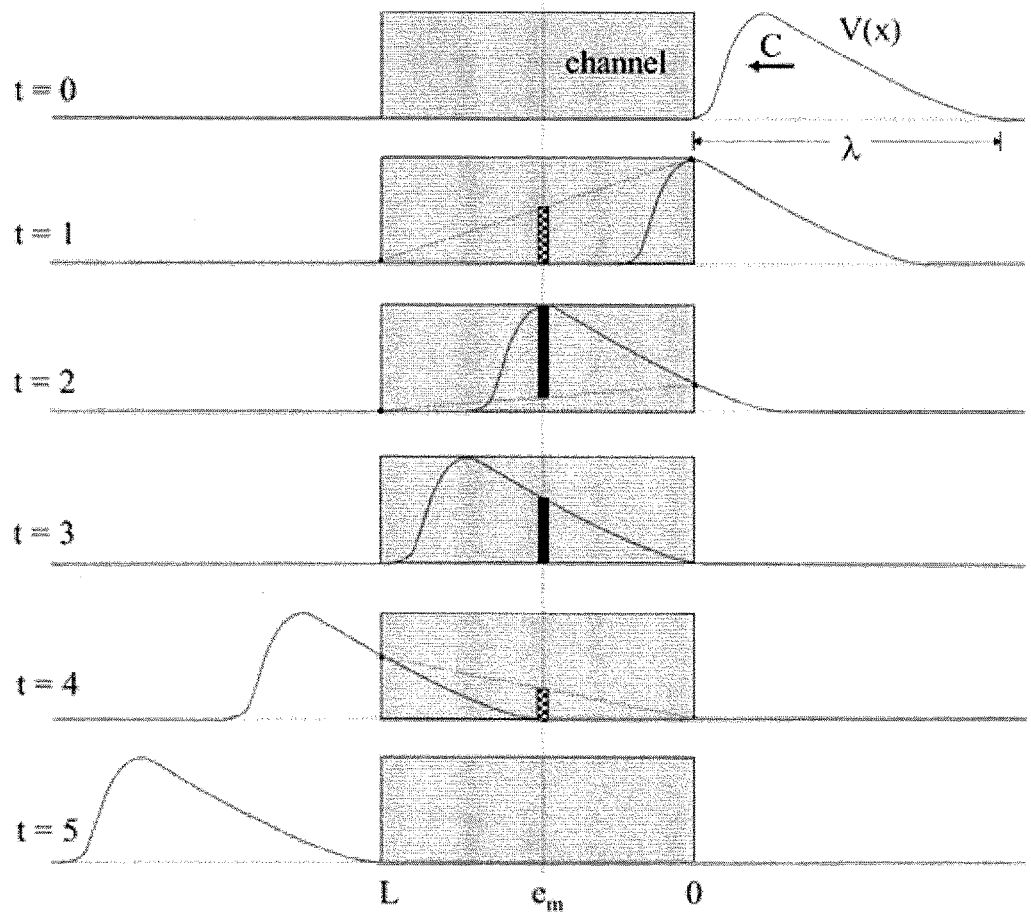
FIG. 5A shows six plots of the $2^{nd}$ Difference spatial profile shown at six sequential time points.
Figure 5B:
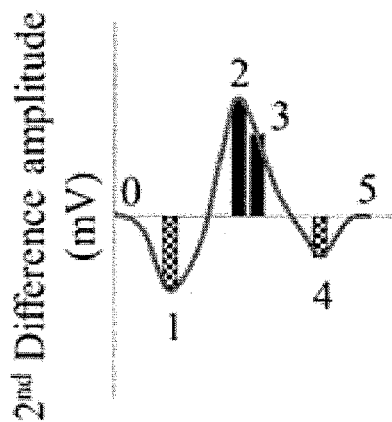
FIG. 5B shows a plot of the triphasic shape of the $2^{nd}$ Difference temporal profile.
Figure 5C:
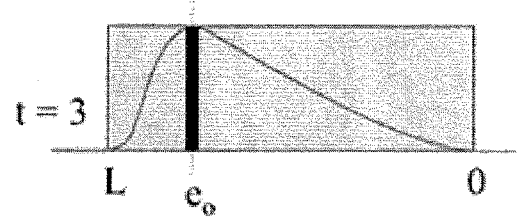
FIG. 5C is a plot showing the $2^{nd}$ Difference for an optimally-placed off-center electrode equals 100% of the AP peak when the AP lies entirely within the channel.

FIG. 5 presents a graphical approach for computing the $2^{nd}$ Difference, which demonstrates the effect of electrode placement on the maximum amplitude of the extracellular signal to be recorded. FIG. 5A depicts 6 time points as an action potential (AP) travels from right to left through a channel with a recording electrode situated at mid-channel, "$e_m$". The $2^{nd}$ Difference approaches its most negative value when the AP peak is coincident with the right edge of the channel at t=1, because the amplitude of the diagonal line at $e_m$ is maximum while the transmembrane voltage at $e_m$ is zero. When the AP peak lies directly above the electrode at t=2, the $2^{nd}$ Difference approaches its most positive value, but note that it is less than the maximum transmembrane voltage. When the AP trailing edge first falls to zero above the electrode at t=4, the $2^{nd}$ Difference approaches another minimum value since the transmembrane voltage at $e_m$ is zero, while the falling phase at the left edge of the channel is considerably positive, resulting in a diagonal that is greater than zero at $e_m$. The temporal profile of the $2^{nd}$ Difference amplitude is shown in FIG. 5B. Its triphasic shape is characteristic of APs recorded using cuff electrodes. FIG. 5C shows the $2^{nd}$ Difference for an optimally-placed off-center electrode equals 100% of the AP peak when the AP lies entirely within the channel.

At t=3 the transmembrane potential at both ends of the channel are simultaneously zero, which means that the diagonal line connecting the ends has a value equal to zero across the channel. FIG. 5C shows that the $2^{nd}$ Difference would have been equal to 100% of the AP peak had the electrode been located at the off-center location marked as $e_o$. In fact, any electrode positioned between $e_m$ and $e_o$ would yield a larger signal amplitude than what one positioned at $e_m$ would record (see, for example, FIG. 5A at time t=3).

An electrode can be placed at a mid-channel position for channels shorter than twice the length of the APs rising phase; otherwise, the electrode can be placed a distance from the channel exit that is equal to the length of the APs rising phase.

Figure 13A:
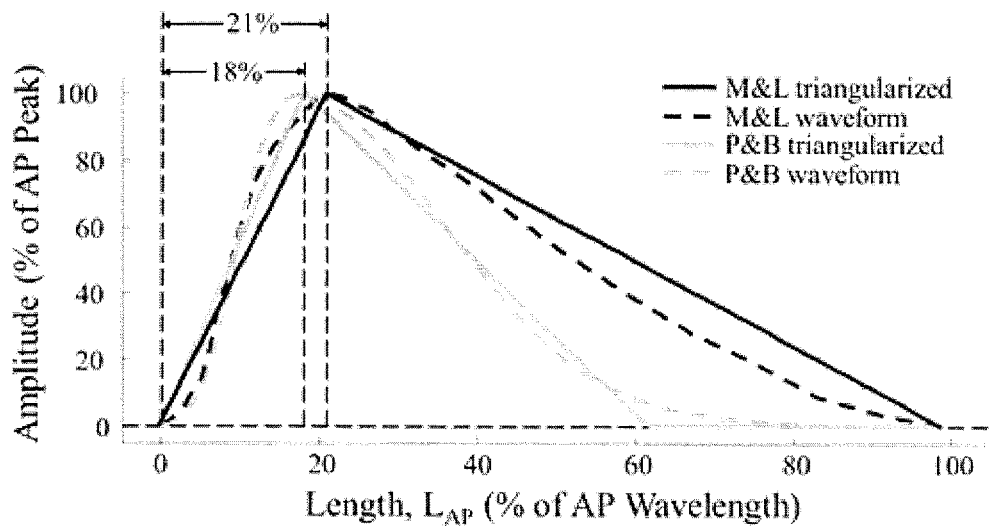
FIG. 13A shows a plot of triangularized nonsymmetrical and symmetric waveforms with rising phases of 21% and 18% $L_{AP}$, respectively.
Figure 13B:
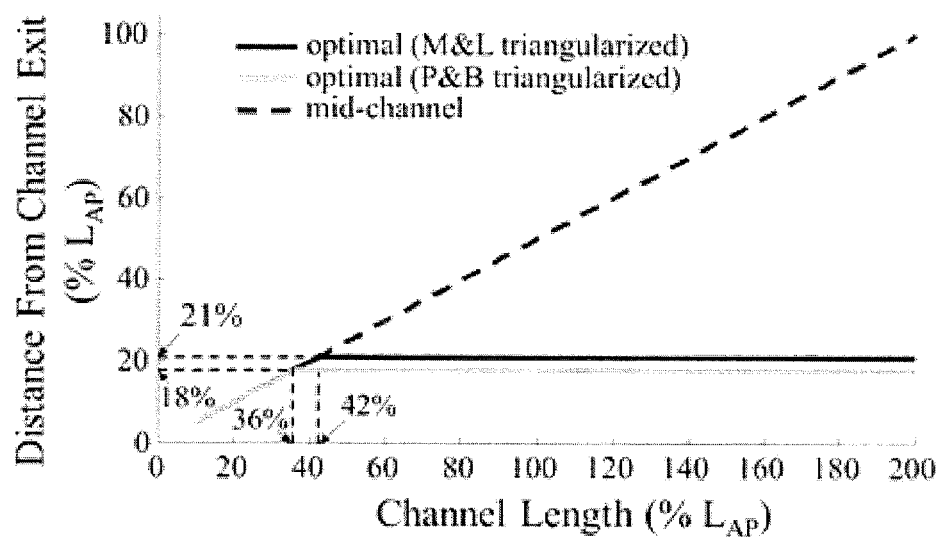
FIG. 13B shows a plot of optimal electrode positions for the triangularized waveforms.

This is supported by the results shown in FIG. 13B, where for each triangularized waveform, the threshold channel length for determining whether the mid-channel or offset electrode position is optimal can be a length equal to twice the length of each APs rising phase. From an electrode design perspective, positing an electrode as described above can be used to identify the ideal electrode position for any channel length and (3) may be used to conservatively estimate the maximum amplitude of the signal one would expect to record.

Since most peripheral nerves are mixed nerves containing thousands of afferent and efferent fibers transmitting action potentials simultaneously in both directions, technologies that can preferentially monitor signals traveling in one direction may be useful for a variety of clinical and research applications. While bipolar electrode configurations can be the simplest approach for doing this, they do not perform as well as the pseudo-tripolar configuration in settings where EMG can easily eclipse recorded neural activity.

Figure 15:
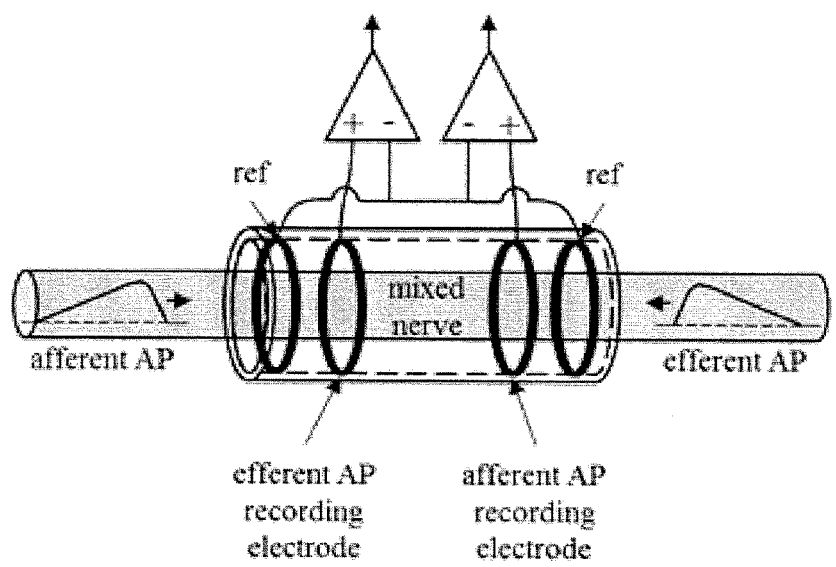
FIG. 15 shows a diagram of a proposed cuff design with two offset electrodes optimally positioned to record afferent and efferent APs traveling asynchronously in a mixed nerve.

For recording both afferent and efferent activity in a mixed nerve, a cuff or microchannel could be outfitted with at least two circumferential recording sites, where the leftmost electrode can be optimally positioned to record a target AP waveform traveling from the right and the right-most electrode can be optimally positioned to record another target AP waveform traveling from the left (FIG. 15).

Balanced pseudo-tripolar electrodes configurations, with the recording electrode situated at mid-channel can provide rejection of large EMG signals external to the implant. However, most pseudo-tripolar electrodes are not truly "balanced". This imbalance, which may be due to imperfect placement of the electrode, spatial variations in extracellular resistance or mismatches in contact impedance, can degrade the common-mode rejection capabilities of the pseudo-tripolar arrangement.

An offset electrode can exacerbate such an imbalance and therefore could further increase susceptibility to common-mode noise. Design modifications have been developed to improve the common-mode rejection, such as a dual-cuff electrode, where an external reference can be sandwiched between the outside of the cuff and another larger cuff and a variable resistor connected between the normally-shorted end contacts. These same design modifications may be beneficial with an offset electrode configuration for applications that require high common-mode rejection. Furthermore, even if the common-mode rejection capability is compromised due to impedance mismatching issues inherent in the unbalanced, offset configurations, their ability to discriminate between APs traveling in opposite directions can be preserved, insofar as the noise from external EMG is smaller than the largest detected neural signal. Finally, thermal, or Johnson, noise could theoretically be reduced using an offset configuration compared to mid-channel placement because the Johnson noise can be proportional to the square root of the resistance path from the recording electrode to the end terminals, which is greatest when the electrode is located at mid-channel.

The methods and processes described herein can be embodied as code and/or data. The software code and data described herein can be stored on one or more machine-readable media (e.g., computer-readable media), which may include any device or medium that can store code and/or data for use by a computer system. When a computer system and/or processor reads and executes the code and/or data stored on a computer-readable medium, the computer system and/or processer performs the methods and processes embodied as data structures and code stored within the computer-readable storage medium.

It should be appreciated by those skilled in the art that computer-readable media include removable and non-removable structures/devices that can be used for storage of information, such as computer-readable instructions, data structures, program modules, and other data used by a computing system/environment. A computer-readable medium includes, but is not limited to, volatile memory such as random access memories (RAM, DRAM, SRAM); and non-volatile memory such as flash memory, various read-only-memories (ROM, PROM, EPROM, EEPROM), magnetic and ferromagnetic/ferroelectric memories (MRAM, FeRAM), and magnetic and optical storage devices (hard drives, magnetic tape, CDs, DVDs); network devices; or other media now known or later developed that is capable of storing computer-readable information/data. Computer-readable media should not be construed or interpreted to include any propagating signals. A computer-readable medium of the subject invention can be, for example, a compact disc (CD), digital video disc (DVD), flash memory device, volatile memory, or a hard disk drive (HDD), such as an external HDD or the HDD of a computing device, though embodiments are not limited thereto. A computing device can be, for example, a laptop computer, desktop computer, server, cell phone, or tablet, though embodiments are not limited thereto.

The subject invention includes, but is not limited to, the following exemplified embodiments.

Embodiment 1

A device for implanting neural interface technology in mammals comprising:

an array of self-closing channels, each channel being defined by a wall of uniform thickness, and each channel wall containing a longitudinal slit along a length of the channel;

each channel including an aperture at each end of the channel; and two flanges that flank the array of channels, the flanges being used to open the self-closing channels.

Embodiment 2

The device of embodiment 1,
the array of the self-closing channels being aligned in parallel.

Embodiment 3

The device according to any of embodiments 1-2,
the aperture of the closed channels having a diameter of from 50 μm to 500 μm.

Embodiment 4

The device according to any of embodiments 1-3,
the channel wall being a width of from 20 μm to 100 μm.

Embodiment 5

The device according to any of embodiments 1-4,
the channels being a length of from 1 mm to 10 mm.

Embodiment 6

The device according to any of embodiments 1-5:
including stem cells and/or Schwann cells into the self-closing channels.

Embodiment 7

The device according to any of embodiments 1-6,
the self-closing channels including a biocompatible elastic material.

Embodiment 8

The device according to any of embodiments 1-7,
the self-closing channels including a porous material.

Embodiment 9

The device according to any of embodiments 1-8, the device further comprising:
chemical and/or biological factors to increase and stabilize regeneration including laminin, chondroitinase, and/or a nerve growth factor (NGF).

Embodiment 10

The device according to any of embodiments 1-9, the device further comprising:
a plurality of cuff electrodes disposed at a circumference of each self-closing channel,
the plurality of cuff electrodes being optimally disposed to detect a maximum amplitude of an action potential signal.

Embodiment 11

A method for determining an optimal position for a cuff electrode on a self-closing channel, the method comprising:
inserting a plurality of cuff electrodes around an axon;
detecting a length of a self-closing channel surrounding an axon;
detecting an extracellular potential signal;
detecting an action potential traveling along the axon;
determining a direction of travel of the action potential signal;
determining a channel entrance and a channel exit,
the channel exit being an end of the channel that the action potential signal enters,
the channel exit being an end of the channel that the action potential exits;
detecting a length of the action potential signal; and
detecting a maximum amplitude of the action potential signal.

Embodiment 12

The method according to embodiment 11,
the extracellular potential at a position x, being determined by the following expression:

$$v(x) = -\frac{R_e}{R_i}\left[V(x) - \left(1 - \frac{x}{L}\right)V(0) - \left(\frac{x}{L}\right)V(L)\right]$$

where v(x) is the extracellular potential at axial position x, V(x) is the transmembrane potential of the active fiber within the channel at position x, V(0) and V(L) are the transmembrane voltages at the channel's entrance and exit, respectively, L is the channel length, $R_e$ is the longitudinal resistance of the extracellular media surrounding the active fiber, and $R_i$ is the longitudinal resistance of the active fiber's axoplasm.

Embodiment 13

The method according to embodiment 12,
the optimal position of a cuff electrode being determined by the following expression:

$$\text{target potential} = V(x) - \left(\frac{V(L) - V(0)}{L}x + V(0)\right)$$

the target potential being at a highest positive value at the optimal position x, and
the cuff electrode being disposed at position x.

Embodiment 14

The method according to any of embodiments 11-12,
the length of channel being shorter than twice the length of the action potential rising phase; and
disposing a first cuff electrode at a distance 50% of the length of the channel.

Embodiment 15

The method according to any of embodiments 11-13,
the length of channel being greater than or equal to twice the length of the action potential rising phase; and
disposing a second cuff electrode at the optimal position x.

Embodiment 16

The method according to any of embodiments 11-12,
a cuff electrode being disposed at a distance equal to 20% of the length of the action potential signal from the channel exit.

Embodiment 17

The method according to any of embodiments 11-12,
a cuff electrode being disposed at a distance equal to 21% of the length of the action potential signal from the channel exit.

Embodiment 18

The method according to any of embodiments 11-17,
a third cuff electrode being used as reference electrode, for unidirectional stimulation, and for stimulation and conduction blocking purposes.

Embodiment 19

The method according to any of embodiments 11-18,
a left-most electrode being optimally positioned to record a target extracellular waveform traveling from the right and a right-most electrode being optimally positioned to record a target extracellular waveform traveling from the left.

A greater understanding of the present invention and of its many advantages may be had from the following examples, given by way of illustration. The following examples are illustrative of some of the methods, applications, embodiments and variants of the present invention. They are, of course, not to be considered as limiting the invention. Numerous changes and modifications can be made with respect to the invention.

It should be understood that the examples and embodiments described herein are for illustrative purposes only and that various modifications or changes in light thereof will be suggested to persons skilled in the art and are to be included within the spirit and purview of this application.

Examples 1-2 described below illustrate exemplary embodiments of the method of the subject invention involving the use of a synthetic floral odor blend as a chemical attractant in insect traps. These exemplary embodiments should not be construed as limiting the scope of the subject invention.

Example 1

Provided in embodiments of the subject invention are methods of manufacturing the claimed device. In a specific embodiment, the device can be made by hand. In another embodiment, the manual techniques can be adapted for automated manufacturing methods.

Prototypes of the claimed device were made by arranging narrow silicone tubes in parallel and embedding them in off-the-shelf clear silicone caulk. Once the device was cured, a metal syringe that had been ground down on one side was inserted into each channel and a razor was used to create a slit through the silicone wall of each tube, using the cupped surface of the syringe as a guide for the razor, as well as for a backing to prevent the razor from cutting all the way through the channel.

Example 2

An FSMA rootlet interface was developed to record from multiple, artificial "rootlets," dissected from L4-L6 lumbar dorsal roots in rats. Custom microchannel electrode arrays were developed by gluing together 8 mm long silicone tubes having inside diameters of 310 μm. Tubes were slit longitudinally and opened along their entire length by pulling on flanges connected to both sides of the array to facilitate nerve insertion and reduce trauma. Pt/Ir and stainless steel recording electrodes were inserted into each channel. Silver wires at both ends of the array were used as a reference electrode for all channels. L4-L6 dorsal roots were exposed by removing the dorsal and lateral processes of T13L3vertebra in SpragueDawley rats and a portion of each root (i.e., "rootlet") was dissected and implanted into the microchannel array.

A variety of cutaneous stimuli were applied using an instrumented von Frey device. The leg joints were also moved independently and simultaneously. Raw signals were amplified (10,000×), bandpass filtered (0.310 kHz) and amplified at 50 kHz. An audioscope was used to monitor real-time activity in each channel. Preliminary results demonstrated that activity in specific channels corresponded to stimuli applied to specific skin regions. As expected, the more rostral the emergence of the recorded "rootlet," the more proximal the skin zone that activated it. Leg movement produced activity in the majority of recordings in which responses to cutaneous stimuli were detected. The RI concept appears to be a viable method to localize stimuli applied to different regions of the hindlimb.

Figure 3A:
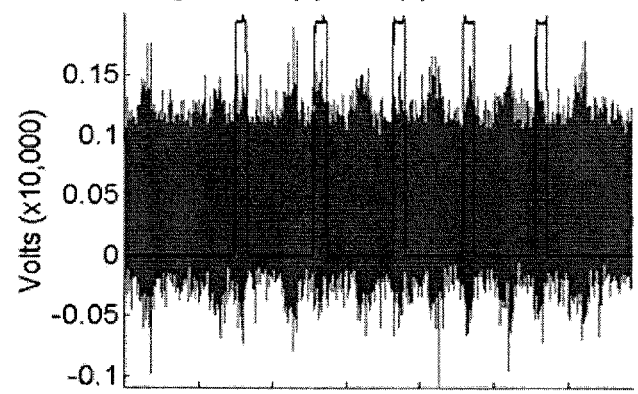
FIG. 3A shows a plot of neural activity recorded by a 200 µm channel when skin fields of the top of a rat subject's foot were stroked with a gauze-tipped applicator, according to an embodiment of the invention.
Figure 3B:
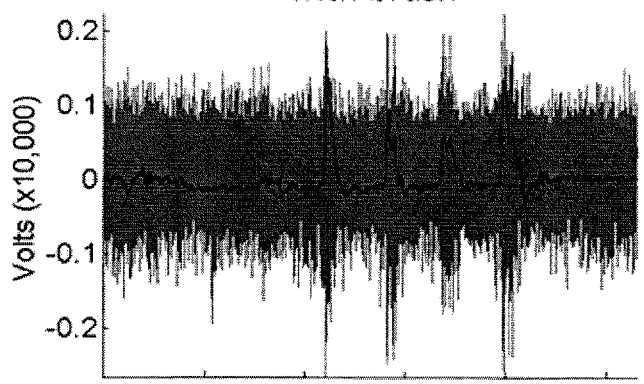
FIG. 3B shows a plot of neural activity recorded by a 500 µm channel when skin fields of the bottom of a rat subject's foot were stroked with a gauze-tipped applicator, according to an embodiment of the invention.
Figure 4:
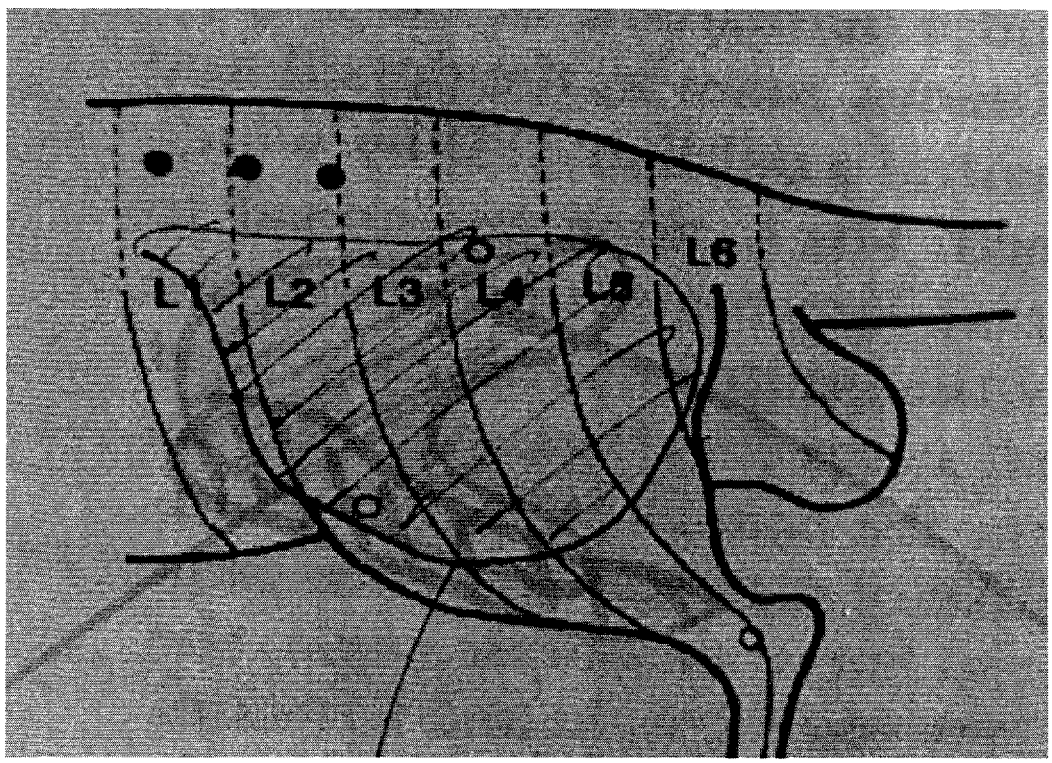
FIG. 4 shows a diagram of tactile skin fields of a subject rat that were innervated by ½ (green), ¼ (orange), and ⅛ (pink) of left L4 root, according to an embodiment of the invention.

The flanged design can facilitate implantation of up to three nerve strands simultaneously. As shown in FIGS. 3A and 3B, arrays recorded neural activity in lumbar roots and teased nerve strands in rats with an SNR of approximately 2. As depicted in FIG. 4, small teased lumbar root fractions were shown to innervate overlapping skin regions.

Example 3

Figure 6A:
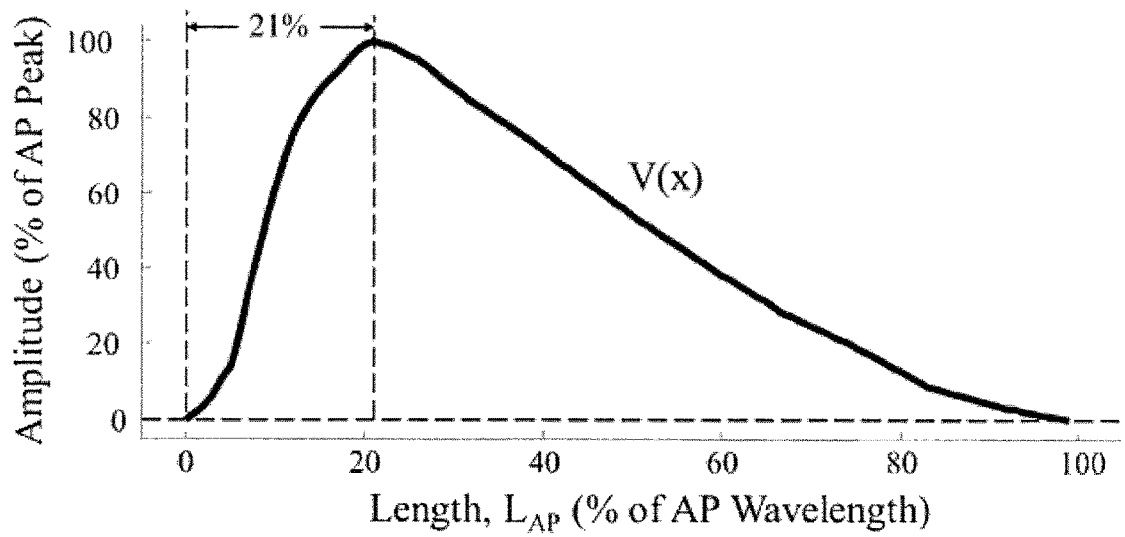
FIG. 6A shows a plot of a nonsymmetrical AP waveform normalized by its peak amplitude and wavelength, $L_{AP}$, respectively.

The action potential waveform shown in FIG. 6A was used in the examples described below. It represents the spatial profile of a realistic AP. It was normalized to 100% of its peak amplitude and 100% of its wavelength, $L_A$, to enable APs of different shapes to be readily compared, independent of their actual amplitudes or wavelengths.

Figure 6B:
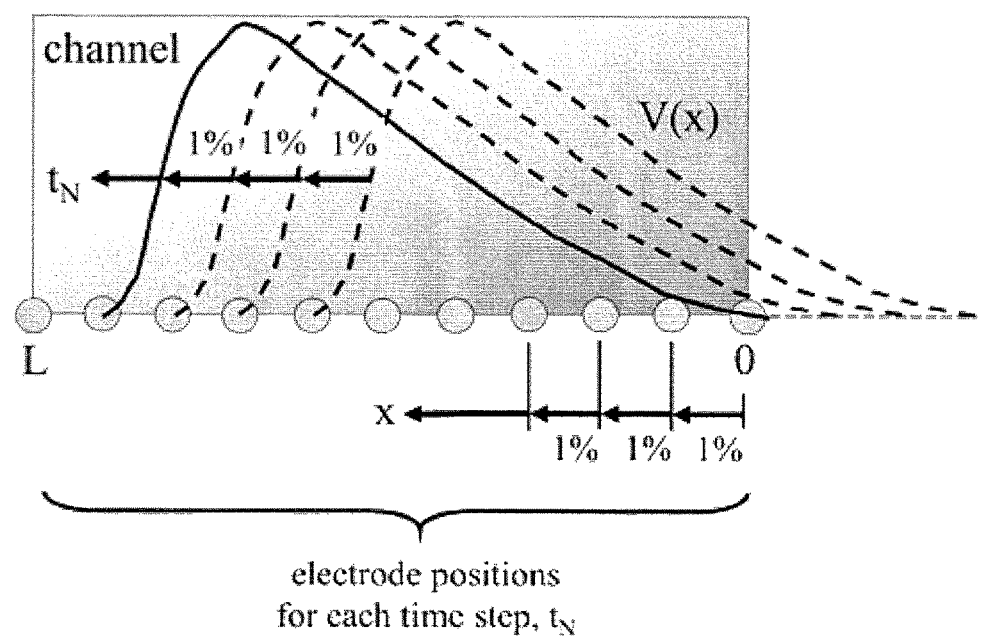
FIG. 6B shows a plot where the $2^{nd}$ Difference was computed for all possible electrode positions within the channel at each time point, $t_N$, as the AP waveform was incrementally stepped through it.

Simulations were performed to identify the electrode position that resulted in the maximum signal amplitude (i.e. the $2^{nd}$ Difference amplitude) for channels ranging in length from 10-200% $L_{AP}$. For each channel length, the nonsymmetrical waveform was incrementally advanced from right to left through the channel in "time" steps of 1% $L_{AP}$ (FIG. 6B). Electrode position was varied from x=0 to x=L in increments of 1% $L_{AP}$ and included the mid-channel position. At each time step, (2) was used to compute the $2^{nd}$ Difference for all possible electrode positions within the channel as shown in FIG. 6B. The electrode position that recorded the largest peak in the $2^{nd}$ Difference was identified as the optimal position. The optimal position, the maximum $2^{nd}$ Difference computed at the optimal position, and the maximum $2^{nd}$ Difference computed at mid-channel served as the three output variables for each simulated channel length.

The potential benefit of using an off-center location was characterized by comparing signals obtained with the electrode at its optimal location to those obtained with the electrode at mid-channel.

Figure 7:
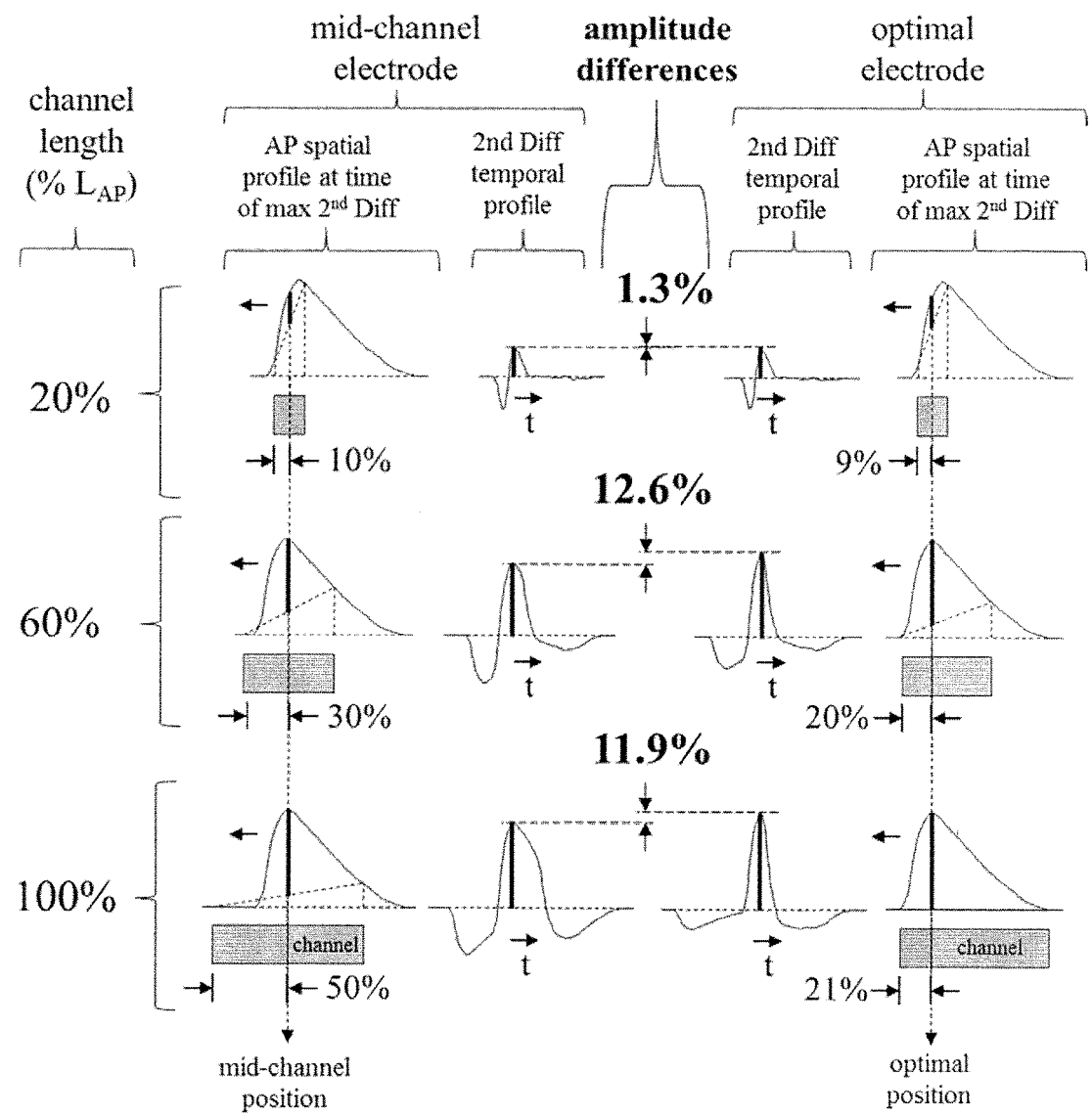
FIG. 7 shows an illustration of a comparison of signals recorded at mid-channel and optimal electrode positions.

FIG. 7 presents the $2^{nd}$ Difference profiles generated when the nonsymmetrical waveform action potential is simulated as traveling from right to left through channels of three different lengths: 20%, 60%, and 100% $L_{AP}$. For each channel length, the maximum signal amplitude recorded with the electrode positioned at mid-channel is compared to that obtained with it in its optimal position.

For short channels, the optimal electrode position can be at mid-channel. For longer channel lengths, the optimal position can be off-center and towards the channel exit. This can be seen for channel lengths of 60% $L_{AP}$, where the optimal electrode position is 20% $L_{AP}$ from the channel exit and provides a peak output signal that exceeds the one recorded at mid-channel by 12.6% $AP_{PEAK}$. The optimal electrode position remains at about the same location for channels exceeding 60% $L_{AP}$; for a channel length of 100% $L_{AP}$, the electrode is optimally positioned at 21% $L_{AP}$ from the channel exit.

Figure 8A:
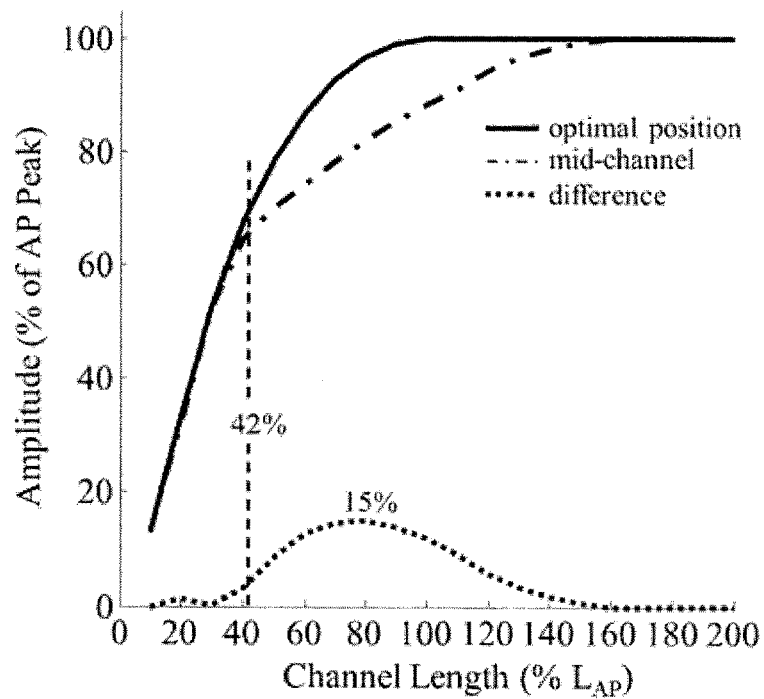
FIG. 8A shows a plot of the maximum $2^{nd}$ Difference amplitude plotted over a range of channel lengths for mid-channel (dash-dot) and optimal (solid) electrode locations, with their difference indicated (dotted).

FIG. 8 extends the results shown in FIG. 7 over a wide range of channel lengths and demonstrates the effect of channel length on recorded signal amplitudes for the mid-channel and optimal offset configurations. For channel lengths ranging between 40-150% $L_{AP}$, the optimal position produces greater signal amplitudes compared to the mid-channel position (see, for example, FIG. 8A). The difference in signal amplitude between the centered and optimal, off-center, electrode configuration reaches a maximum of 15% of the AP peak for channel lengths of about 80% $L_{AP}$. The vertical dashed line located at 42% $L_{AP}$ is twice the spatial spread of the rising phase of the AP waveform and marks the shortest channel length at which the optimal position diverges from the mid-channel position; for channels shorter than this length, the mid-channel position is optimal.

Figure 8B:
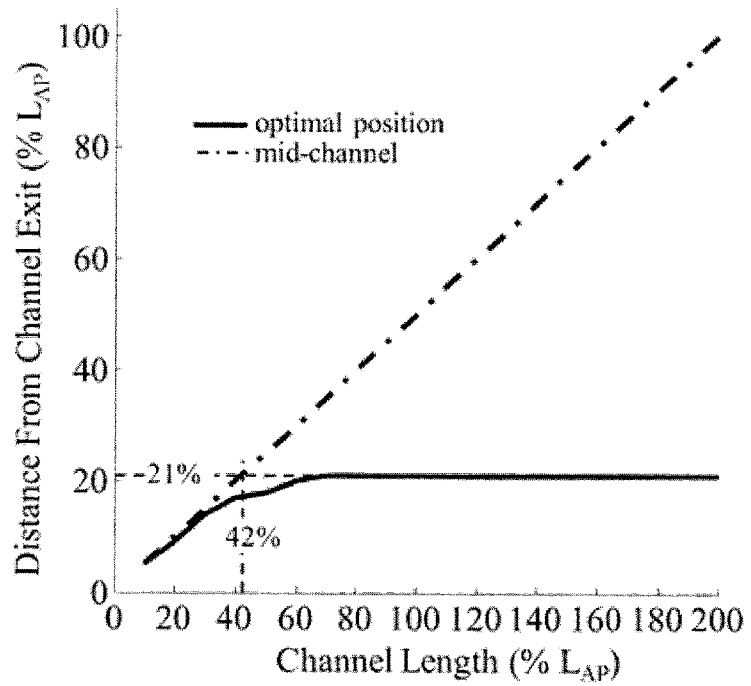
FIG. 8B shows a plot of the optimal and mid-channel electrode positions over a range of channel lengths.

FIG. 8B shows the distance from the channel exit to the electrode for mid-channel and optimal electrode positions over the same range of channel lengths. For channel lengths less than 42% $L_{AP}$, the optimal position is at or close to mid-channel. For longer channels, the optimal position approaches and remains constant at a distance of 21% $L_{AP}$ from the channel exit, equal to the rising phase of the nonsymmetrical waveform (see, for example, FIG. 6A).

Example 4

The ability of the off-center placement to preferentially record signals traveling in a "target" direction was investigated by characterizing the extent to which the ideal electrode placement would attenuate the recorded signal for APs traveling in a direction opposite the target one.

Figure 9:
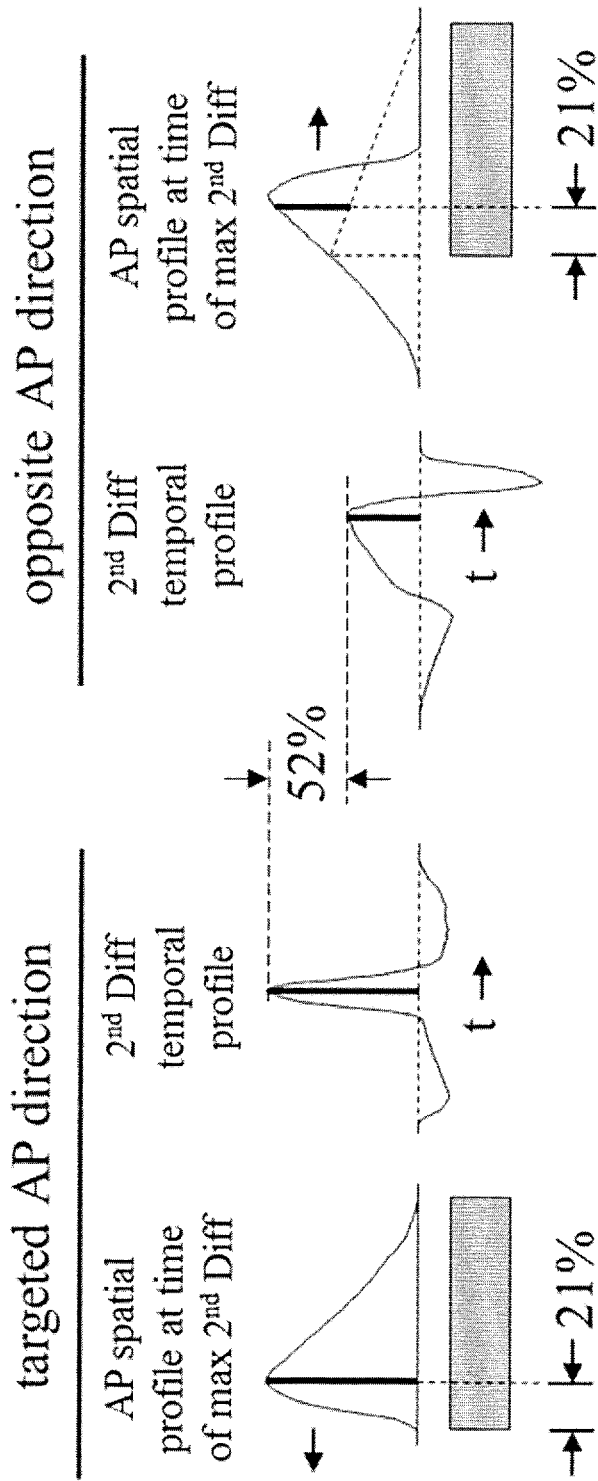
FIG. 9 shows an illustration of recording of target AP versus an AP traveling in the opposite direction.

In FIG. 9A, an electrode located at 21% $L_{AP}$ from the channel exit is optimally configured to record the AP propagating in the "target" direction from right to left. While the offset configuration can be ideally suited to record the target AP, it can be a comparatively poor configuration for recording the same AP traveling in the opposite direction, where the recorded signal is reduced to about 50% of that obtained for the AP traveling in the target direction (see, for example, FIG. 9B).

Additionally, the temporal profiles of the recorded signals differ noticeably. For APs traveling in the target direction, the $2^{nd}$ Difference profile in time can be characterized by a large central positive peak flanked by two smaller negative phases. For APs traveling in the opposite direction, the $2^{nd}$ Difference temporal profile can be characterized by a reduced positive peak that is more spread-out in time and is flanked by a small negative phase and a much larger negative phase that has an amplitude nearly equivalent to that of the positive one.

Figure 10:
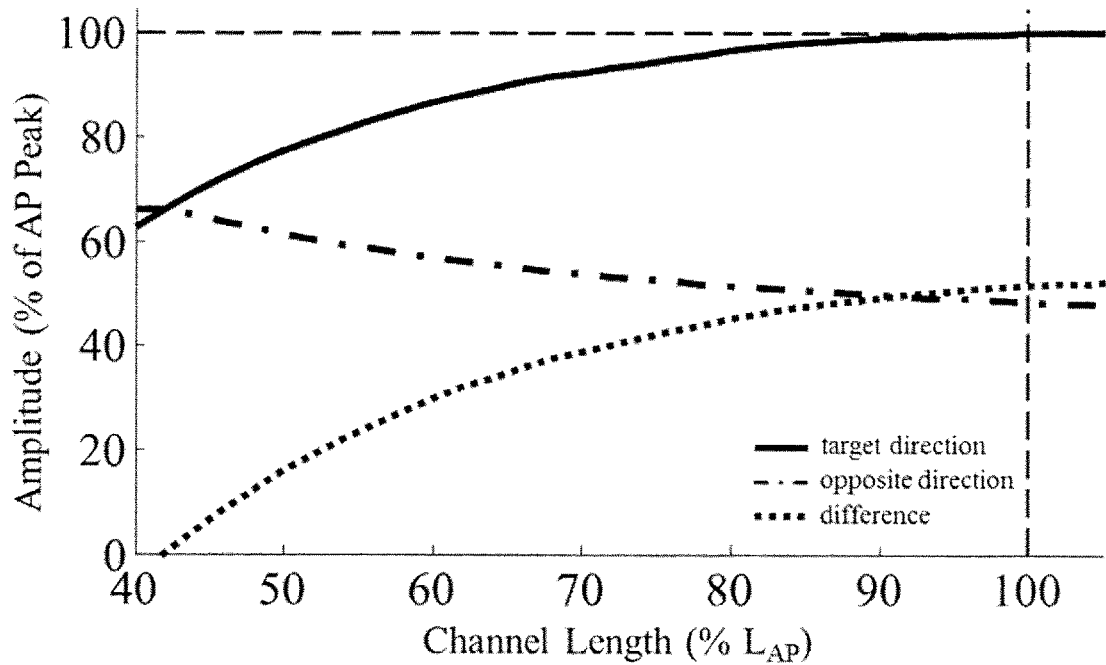
FIG. 10 shows a plot of the maximum $2^{nd}$ Difference amplitude plotted over a range of channel lengths for equivalent APs traveling in the target (solid) and opposite (dash-dot) directions.

The effect of channel length on recorded signal amplitudes for the AP traveling in the target and opposite directions is summarized in FIG. 10 for channels longer than 40% $L_{AP}$. Only channels exceeding 40% $L_{AP}$ were included for this analysis, since the optimal electrode position is located at mid-channel for channel lengths shorter than this (see, for example, FIG. 8). For longer channel lengths, the offset configuration results in a progressive enhancement of the signal for APs traveling in the target direction and attenuation for APs travelling in the opposite direction. The flattening of the curves near lengths of 100% $L_{AP}$ suggests channels longer than the AP wavelength do not provide additional discriminating ability.

Figure 11:
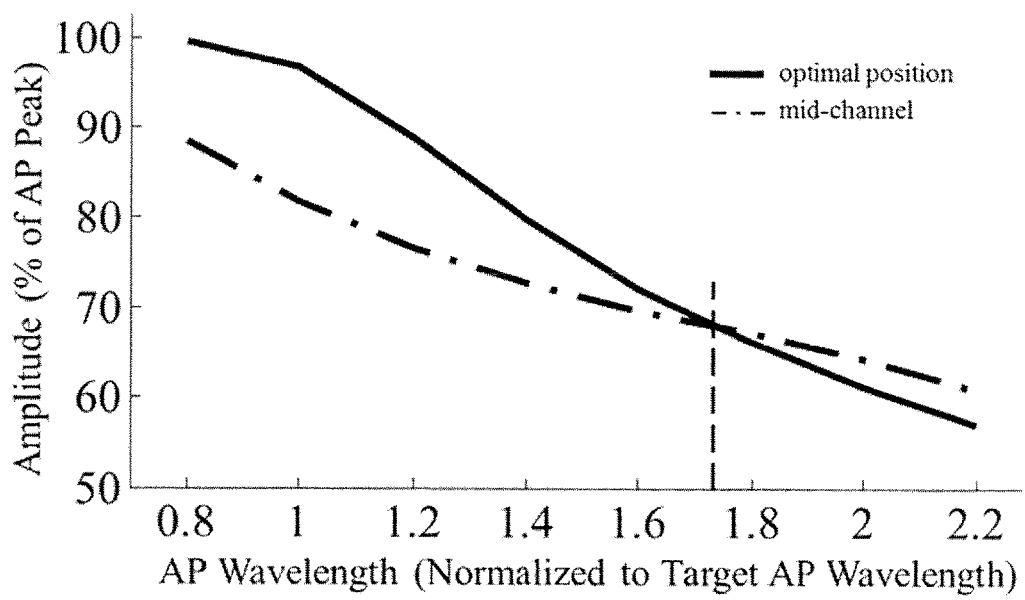
FIG. 11 shows a plot of the maximum $2^{nd}$ Difference amplitudes plotted against AP wavelength for mid-channel and optimal electrode locations.

Since the wavelengths of actual APs can be longer or shorter than the target wavelength used to specify the optimal electrode position, we investigated the sensitivity of the recording advantage gained by an off-center configuration to variations in AP wavelength. FIG. 11 shows the effect of AP wavelength on the amplitude of recorded signals for the centered and off-centered electrode configurations. All output signals were computed using a channel length of 80% $L_{AP}$. For all wavelengths less than approximately 1.7 times that of the target (indicated by the dashed vertical line), the optimal configuration performs better than an electrode at mid-channel.

Example 5

Figure 12A:
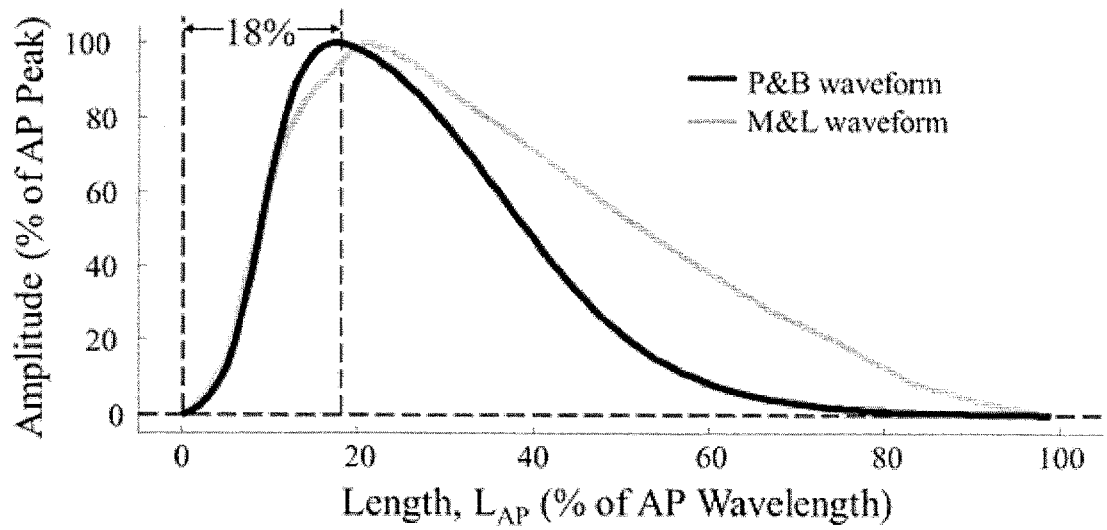
FIG. 12A shows a plot of a symmetric waveform with a rising phase of 18% $L_{AP}$.
Figure 12B:
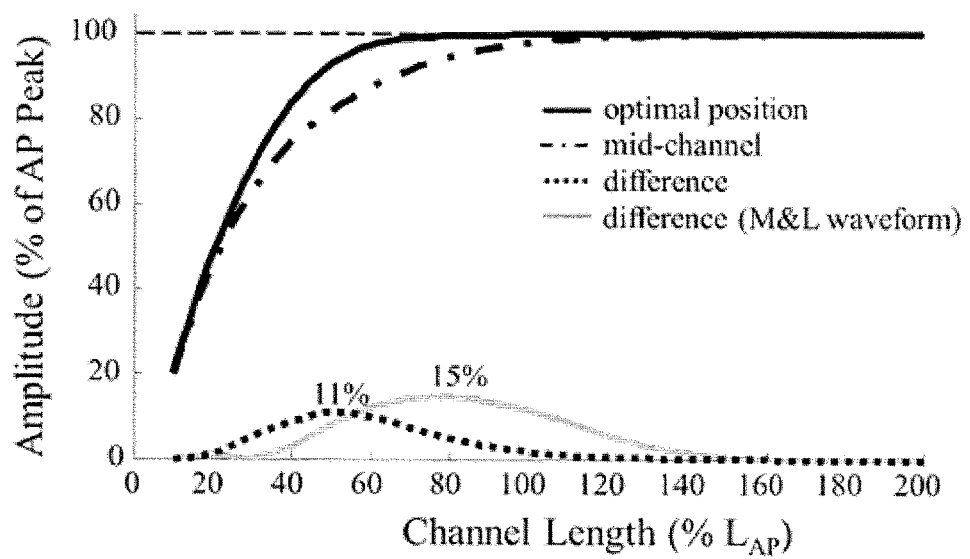
FIG. 12B shows a plot of the maximum $2^{nd}$ Difference amplitudes for a symmetric waveform shown over a range of channel lengths for the mid-channel (dash-dot) and optimal (solid) electrode locations, with their difference (dotted).

The effect of AP symmetry was examined using a symmetric waveform. The waveform is more symmetric about its peak due to the comparatively shorter duration of its falling phase compared to the nonsymmetrical waveform, as shown in FIG. 12A. As was seen for the nonsymmetrical waveform, the offset configuration is superior to the mid-channel position over a wide range of channel lengths (see, for example, FIG. 12B). Compared to the nonsymmetrical waveform, however, the differences between the optimal and mid-channel positions in recorded signal amplitudes can be less, which can be seen in FIG. 12B where the separation between the solid and dash-dot black traces is less than what was observed for the nonsymmetrical waveform (see, for example, FIG. 8). The amplitude difference of the output signal between the optimal and mid-channel configurations reaches a maximum of 11% $AP_{PEAK}$ for the symmetric waveform compared to 15% $AP_{PEAK}$ for the nonsymmetrical waveform (see, for example, FIG. 8B).

Example 6

FIG. 13A shows piecewise linear, or "triangularized", approximations of the nonsymmetrical and symmetric waveforms, where the lengths of their rising phases remain identical to those of the original waveforms. FIG. 13B shows that the optimal electrode position is a distance equal to the length of each waveform's rising phase from the channel exit for channels that exceed twice the rising phase in length. Thus, the optimal electrode position remains a distance of 21% $L_{AP}$ from the exit for channel lengths that exceed 42% $L_{AP}$ (=2×21% $L_{AP}$) for the nonsymmetrical triangularized waveform and 18% $L_{AP}$ for channel lengths that exceed 36% $L_{AP}$ (=2×18% $L_{AP}$) for the symmetric triangularized waveform. For channels shorter than this threshold length, the mid-channel position is optimal, shown in FIG. 13B where the optimal electrode position for each waveform overlaps the mid-channel position (dashed line).

Example 7

Figure 14:
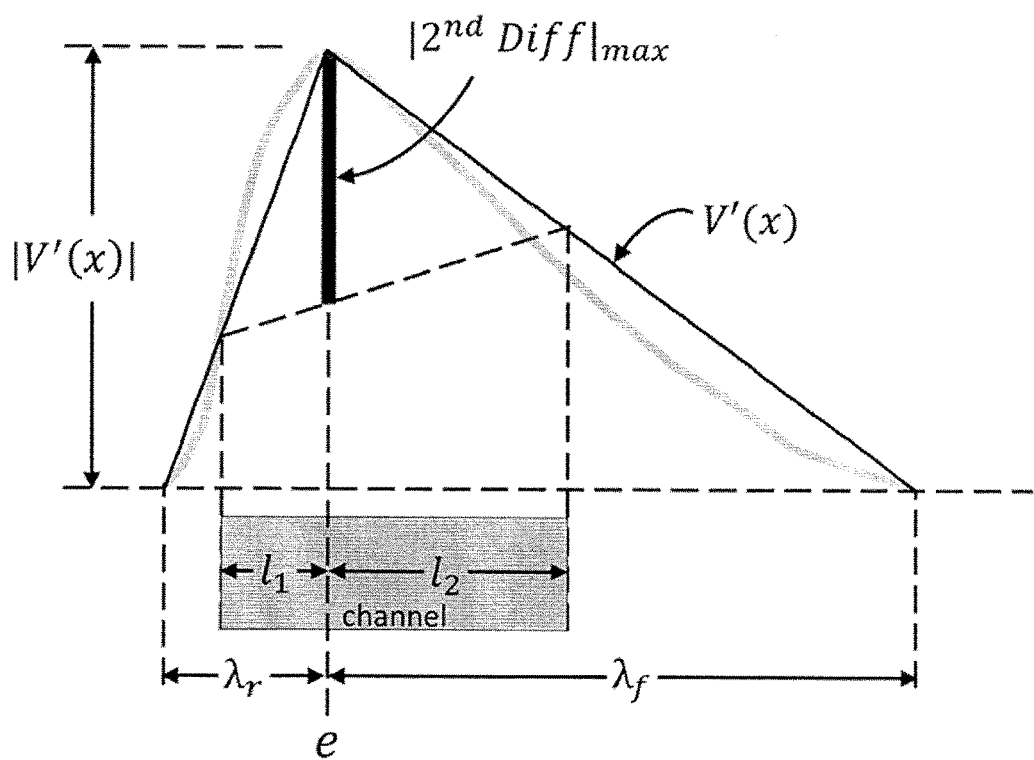
FIG. 14 shows a diagram illustrating the maximum $2^{nd}$ Difference for an electrode "e" located a distance $l_1$ and $l_2$ from the channel exit and entrance, respectively, may be computed for any triangularized AP, characterized by its peak amplitude, $|V'(x)|$, and rising and falling phase lengths of $\lambda_r$ and $\lambda_f$, respectively.

Explicit expressions for the maximum $2^{nd}$ Difference amplitude for any length cuff, electrode position and AP waveform may be derived if APs are approximated as triangular waveforms. FIG. 14 shows the three parameters needed to linearize an AP waveform: its height, $|V(x)|$ and the lengths of its rising and falling phases, A $\lambda_r$ and $\lambda_f$, respectively. For an electrode "e" lying directly beneath the AP peak and located a distance $l_1$ and $l_2$ from the channel's exit and entrance, respectively, the maximum $2^{nd}$ Difference may be expressed explicitly in terms of these parameters as:

$$|2^{nd}\, Diff|_{max} = |V'(x)| \cdot \frac{l_1 l_2}{l_1 + l_2} \cdot \frac{\lambda_r + \lambda_f}{\lambda_r \lambda_f} \qquad (3)$$

(where $l_1 \leq \lambda_r$ and $l_2 \leq \lambda_f$)

The utility of (3) may be appreciated if one uses it to verify the maximum $2^{nd}$ Difference amplitude for the electrode "$e_o$" depicted in FIG. 5C. Here, $l_1 = \lambda_r$ and $l_2 = \lambda_f$.

trend can be seen for the slow-conducting fiber. To record the maximum amplitude from a waveform similar in shape to the nonsymmetrical waveform (rising phase ~20 $L_{AP}$ of the falling phase), a mid-channel placement of the electrode would necessitate a channel length of ~160% $L_{AP}$, approximately 60% longer that the length required with an optimal offset location. In addition, the longer channel with a mid-channel configuration would record the same amplitude if the waveform were traveling in the opposite direction. Thus, the offset configuration affords an opportunity to record the maximum signal possible using the shortest channel length possible and would provide additional advantages for selective recordings from mixed nerves.

TABLE 1

Minimum channel lengths needed to achieve maximum possible signal amplitudes.

| Speed[a] C (mm/ms) | Rise time[a] $T_r$ (ms) | Fall time[a] $T_f$ (ms) | Duration[1] $T_d$ (ms) | Length of rising phase $\lambda_r$ (mm) | Length of falling phase $\lambda_f$ (mm) | Threshold length $2\lambda_r$ (mm) | Min. length for electrode at mid-channel $2\lambda_f$ (mm) | Min. length for electrode optimally positioned at $\lambda_r$ $\lambda$ (mm) |
|---|---|---|---|---|---|---|---|---|
| 16 | 0.13 | 0.35 | 0.48 | 2.1 | 5.6 | 4.2 | 11.2 | 7.7 |
| 64 | 0.10 | 0.26 | 0.36 | 6.4 | 16.6 | 12.8 | 33.2 | 23.0 |

[a]Speed and temporal data taken from Paintal AP (1966)

Making these substitutions into (3) yields $|V'(x)|$ as the maximum amplitude of the $2^{nd}$ Difference for all times as the AP traverses the channel. When used to estimate signal amplitudes, (3) predicted the maximum recorded amplitude to within 5% of those obtained for the nonsymmetrical waveform for most channel lengths. The largest discrepancy of 7% $AP_{PEAK}$ occurred at a channel length of 32% $L_{AP}$, too short to warrant an off-center electrode placement Temporal parameters can be used to characterize action potentials; the corresponding spatial parameter of the action potential may be determined by multiplying its corresponding temporal analog by the speed of AP propagation, C. Thus, substituting these expressions for $\lambda_r$ and $\lambda_f$ into (3) yields:

$$\lambda_r = C \cdot T_r \qquad (4)$$

$$\lambda_f = C \cdot T_f \qquad (5)$$

Substituting these expressions for $\lambda_r$ and $\lambda_f$ into (3) yields:

$$|2^{nd}\, Diff|_{max} = \frac{|V'(x)|}{C} \cdot \frac{l_1 l_2}{l_1 + l_2} \cdot \frac{T_r + T_f}{T_r T_f} \qquad (6)$$

Example 6

Table 1 gives optimal offset dimensions for a slow (16 mm/ms) and a fast (64 mm/ms) AP recorded from the vagus and saphenous nerves in cats. An electrode positioned 6.4 mm from the channel exit would be optimal for channels exceeding a threshold length of 12.8 mm for the fast-conducting fiber. The maximum possible signal to be recorded would be achieved for channel lengths equal to at least the AP wavelength of 23 mm. This is over 10 mm shorter than the minimum channel length of 33.2 mm required for a mid-channel configuration to record an equivalent signal, since a mid-channel electrode will only record the maximum signal amplitude possible for channels at least twice the length of the APs falling phase. A similar All patents, patent applications, provisional applications, and publications referred to or cited herein (including those in the "References" section) are incorporated by reference in their entirety, including all figures and tables, to the extent they are not inconsistent with the explicit teachings of this specification.

REFERENCES

[1] Brindley, G. 1977. An implant to empty the bladder or close the urethra. Journal of Neurology, Neurosurgery & Psychiatry, 40, 358-369.

[2] Fitzgerald, J. J., Lacour, S. P., McMahon, S. B. & Fawcett, J. W. 2008. Microchannels as axonal amplifiers. IEEE Transactions on Biomedical Engineering, 55, 1136-1146.

[3] Haugland, M. K. & Sinkjaer, T. 1995. Cutaneous whole nerve recordings used for correction of footdrop in hemiplegic man. IEEE Transactions on rehabilitation Engineering, 3, 307-317.

[4] Hoffer, J. A. & Kallesoe, K. 2001. How to use nerve cuffs to stimulate, record, or modulate neural activity. Neural Prostheses for Restoration of Sensory and Motor Function, 139-78.

[5] Marks, W. B. & Loeb, G. E. 1976. Action currents, internodal potentials, and extracellular records of myelinated mammalian nerve fibers derived from node potentials. Biophysical journal, 16, 655-668.

[6] Meier, J. H., Rutten, W. L. & Boom, H. B. 1998. Extracellular potentials from active myelinated fibers inside insulated and noninsulated peripheral nerve. IEEE transactions on biomedical engineering, 45, 1146-1153.

[7] Paintal, A. 1966. The influence of diameter of medullated nerve fibres of cats on the rising and falling phases of the spike and its recovery. The Journal of physiology, 184, 791-811.

[8] Plonsey, R. & Barr, R. C. 2007. Bioelectricity: a quantitative approach, Springer Science & Business Media.

[9] Popovic, D. B., Stein, R. B., Jovanovic, K. L., Dai, R., Kostov, A. & Armstrong, W. W. 1993. Sensory nerve recording for closed-loop control to restore motor functions. IEEE transactions on biomedical engineering, 40, 1024-1031.
[10] Sahin, M., Haxhiu, M. A., Durand, D. M. & Dreshaj, I. A. 1997. Spiral nerve cuff electrode for recordings of respiratory output. Journal of Applied Physiology, 83, 317-322.
[11] Sinkjaer, T. 2000. Integrating sensory nerve signals into neural prosthesis apparatuses. Neuromodulation: Technology at the Neural Interface, 3, 34-41.
[12] Stein, R., Gordon, T., Hoffer, J., Davis, L. & Charles, D. 1980. Long-term recordings from cat peripheral nerves during degeneration and regeneration: implications for human nerve repair and prosthetics. Nerve Repair: Its Clinical and Experimental Basis, 166-176.
[13] Stein, R. & Pearson, K. 1971. Predicted amplitude and form of action potentials recorded from unmyelinated nerve fibres. Journal of theoretical biology, 32, 539-558.
[14] Stein, R. B., Charles, D., Davis, L., Jhamandas, J., Mannard, A. & Nichols, T. 1975. Principles underlying new methods for chronic neural recording. Canadian Journal of Neurological Sciences/Journal Canadien des Sciences Neurologiques, 2, 235-244.
[15] Stein, R. B., Nichols, T., Jhamandas, J., Davis, L. & Charles, D. 1977. Stable long-term recordings from cat peripheral nerves. Brain research, 128, 21-38.
[16] Struijk, J. J. 1997. The extracellular potential of a myelinated nerve fiber in an unbounded medium and in nerve cuff models. Biophysical journal, 72, 2457.
[17] Struijk, J. J. & Thomson, M. Tripolar nerve cuff recording: stimulus artifact, EMG and the recorded nerve signal. Engineering in Medicine and Biology Society, 1995., IEEE 17th Annual Conference, 1995. IEEE, 1105-1106.
[18] Struijk, J. J., Thomsen, M., Larsen, J. O. & Sinkjaer, T. 1999. Cuff electrodes for long-term recording of natural sensory information. IEEE engineering in medicine and biology magazine, 18, 91-98.

What is claimed is:

1. An implantable device, configured to separate nerve strands in mammals, comprising:
    an array of tubular self-closing channels, the array having a top side,
    each self-closing channel being defined by a wall including a channel wall portion with a longitudinal slit along a length of the top side of each channel and perpendicular to the top side with adjacent wall portions being connected and forming an array of slits;
    each self-closing channel including an aperture at each end; and
    two flanges that flank the array of slits in substantially a common plane with the slits, the flanges being configured to pull the array of slits in opposite directions and simultaneously open all of the longitudinal slits of the array of self-closing channels without substantially bending the flanges relative to one another, such that, when the flanges are pulled to open the slits, nerve strands placed parallel over the longitudinal slits are dropped through the slits and into the channels and, when the flanges are released the slits close, thereby compartmentalizing the nerve strands in the channels.

2. The device of claim 1, the array of the self-closing channels being aligned in parallel.

3. The device of claim 1, the aperture of the closed channels having a diameter of from 50 µm to 500 µm.

4. The device of claim 1, the channel wall being a width of from 20 µm to 100 µm.

5. The device of claim 1, the channels having a length between the apertures of from 1 mm to 10 mm.

6. The device of claim 1, the self-closing channels being adapted to contain at least one of stem cells and Schwann cells.

7. The device of claim 1, the self-closing channels including a biocompatible elastic material.

8. The device of claim 1, the self-closing channels including a porous material.

9. The device of claim 1, further comprising:
    chemical and/or biological factors to increase and stabilize regeneration including laminin, chondroitinase, and/or a nerve growth factor (NGF).

10. The device according to claim 1, wherein the array comprises three or more self-closing channels.

11. A device for implanting neural interface technology in mammals comprising:
    an array of tubular self-closing channels, the array having a top side,
    each self-closing channel being defined by a wall including a channel wall portion with a longitudinal slit along a length of the top side of each channel and perpendicular to the top side with adjacent wall portions being connected and forming an array of slits;
    each self-closing channel including an aperture at each end; and
    two flanges that flank the array of slits in substantially a common plane with the slits, the flanges being configured to pull the array of slits in opposite directions and simultaneously open all the longitudinal slits of the array of self-closing channels without substantially bending the flanges relative to one another, such that, when the flanges are pulled to open the slits, nerve strands placed parallel over the longitudinal slits are dropped through the slits and into the channels and, when the flanges are released the slits close, thereby compartmentalizing the nerve strands in the channels
    a plurality of cuff electrodes disposed at a circumference of each self-closing channel,
    the aperture of the closed channels having a diameter of from 50 µm to 500 µm,
    the channel wall being a width of from 20 µm to 100 µm, and
    the channels being a length of from 1 mm to 10 mm.

12. The device according to claim 11, wherein the array comprises three or more self-closing channels.

* * * * *

UNITED STATES PATENT AND TRADEMARK OFFICE
CERTIFICATE OF CORRECTION

PATENT NO. : 10,286,207 B2
APPLICATION NO. : 15/730892
DATED : May 14, 2019
INVENTOR(S) : Iian Black et al.

It is certified that error appears in the above-identified patent and that said Letters Patent is hereby corrected as shown below:

In the Specification

Columns 7-8,
Lines 56-51, "An offset electrode can exacerbate such an imbalance and therefore could further increase susceptibility to common-mode noise. Design modifications have been developed to improve the common-mode rejection, such as a dual-cuff electrode, where an external reference can be sandwiched between the outside of the cuff and another larger cuff and a variable resistor connected between the normally-shorted end contacts. These same design modifications may be beneficial with an offset electrode configuration for applications that require high common-mode rejection. Furthermore, even if the common-mode rejection capability is compromised due to impedance mismatching issues inherent in the unbalanced, offset configurations, their ability to discriminate between APs traveling in opposite directions can be preserved, insofar as the noise from external EMG is smaller than the largest detected neural signal. Finally, thermal, or Johnson, noise could theoretically be reduced using an offset configuration compared to mid-channel placement because the Johnson noise can be proportional to the square root of the resistance path from the recording electrode to the end terminals, which is greatest when the electrode is located at mid-channel.
    The methods and processes described herein can be embodied as code and/or data. The software code and data described herein can be stored on one or more machine-readable media (e.g., computer-readable media), which may include any device or medium that can store code and/or data for use by a computer system. When a computer system and/or processer reads and executes the code and/or data stored on a computer-readable medium, the computer system and/or processer performs the methods and processes embodied as data structures and code stored within the computer-readable storage medium.
    It should be appreciated by those skilled in the art that computer-readable media include removable and non-removable structures/devices that can be used for storage of information, such as computer-readable instructions, data structures, program modules, and other data used by a computing system/environment. A computer-readable medium includes, but is not limited to, volatile memory such as random access memories (RAM, DRAM, SRAM); and non-volatile memory such as flash memory, various read-only-memories (ROM, PROM, EPROM, EEPROM), magnetic and ferromagnetic/ferroelectric memories (MRAM, FeRAM), and magnetic and optical storage devices Signed and Sealed this
Third Day of September, 2019

Andrei Iancu
*Director of the United States Patent and Trademark Office*

(hard drives, magnetic tape, CDs, DVDs); network devices; or other media now known or later developed that is capable of storing computer-readable information/data. Computer-readable media should not be construed or interpreted to include any propagating signals. A computer-readable medium of the subject invention can be, for example, a compact disc (CD), digital video disc (DVD), flash memory device, volatile memory, or a hard disk drive (HDD), such as an external HDD or the HDD of a computing device, though embodiments are not limited thereto. A computing device can be, for example, a laptop computer, desktop computer, server, cell phone, or tablet, though embodiments are not limited thereto.

The subject invention includes, but is not limited to, the following exemplified embodiments." should read
--An offset electrode can exacerbate such an imbalance and therefore could further increase susceptibility to common-mode noise. Design modifications have been developed to improve the common-mode rejection, such as a dual-cuff electrode, where an external reference can be sandwiched between the outside of the cuff and another larger cuff and a variable resistor connected between the normally-shorted end contacts. These same design modifications may be beneficial with an offset electrode configuration for applications that require high common-mode rejection. Furthermore, even if the common-mode rejection capability is compromised due to impedance mismatching issues inherent in the unbalanced, offset configurations, their ability to discriminate between APs traveling in opposite directions can be preserved, insofar as the noise from external EMG is smaller than the largest detected neural signal. Finally, thermal, or Johnson, noise could theoretically be reduced using an offset configuration compared to mid-channel placement because the Johnson noise can be proportional to the square root of the resistance path from the recording electrode to the end terminals, which is greatest when the electrode is located at mid-channel.

The subject invention includes, but is not limited to, the following exemplified embodiments.--

Column 11,
Lines 30-48, "It should be understood that the examples and embodiments described herein are for illustrative purposes only and that various modifications or changes in light thereof will be suggested to persons skilled in the art and are to be included within the spirit and purview of this application.

Examples 1-2 described below illustrate exemplary embodiments of the method of the subject invention involving the use of a synthetic floral odor blend as a chemical attractant in insect traps. These exemplary embodiments should not be construed as limiting the scope of the subject invention.
EXAMPLE 1
Provided in embodiments of the subject invention are methods of manufacturing the claimed device. In a specific embodiment, the device can be made by hand. In another embodiment, the manual techniques can be adapted for automated manufacturing methods." should read
--It should be understood that the examples and embodiments described herein are for illustrative purposes only and that various modifications or changes in light thereof will be suggested to persons skilled in the art and are to be included within the spirit and purview of this application.
EXAMPLE 1
Provided in embodiments of the subject invention are methods of manufacturing the claimed device. In a specific embodiment, the device can be made by hand. In another embodiment, the manual techniques can be adapted for automated manufacturing methods.--